(12) United States Patent
Seth et al.

(10) Patent No.: US 7,534,481 B2
(45) Date of Patent: May 19, 2009

(54) SHAPED ELASTIC TAB LAMINATES

(75) Inventors: Jayshree Seth, Woodbury, MN (US); Katherine A. Graham, Roseville, MN (US); Brandy S. Nolan, Austin, TX (US)

(73) Assignee: 3M Innovative Properties Company, Saint Paul, MN (US)

( * ) Notice: Subject to any disclaimer, the term of this patent is extended or adjusted under 35 U.S.C. 154(b) by 249 days.

(21) Appl. No.: 11/463,122

(22) Filed: Aug. 8, 2006

(65) Prior Publication Data

US 2008/0038507 A1 Feb. 14, 2008

(51) Int. Cl.
*B32B 3/26* (2006.01)

(52) U.S. Cl. .............. 428/80; 428/172; 428/195.1; 428/201

(58) Field of Classification Search ............... 428/80, 428/172, 195.1, 201; 604/389
See application file for complete search history.

(56) References Cited

U.S. PATENT DOCUMENTS

| | | |
|---|---|---|
| 2,170,560 A | 8/1939 | Hayes |
| 2,787,244 A | 4/1957 | Hicken |
| 2,919,467 A | 1/1960 | Mercer |
| 3,085,292 A | 4/1963 | Kindseth |
| 3,276,944 A | 10/1966 | Levy |
| 3,338,992 A | 8/1967 | Kinney |
| 3,341,394 A | 9/1967 | Kinney |
| 3,386,876 A | 6/1968 | Wyckoff |
| 3,394,431 A | 7/1968 | Nalle, Jr. |
| 3,502,538 A | 3/1970 | Petersen |
| 3,502,763 A | 3/1970 | Hartmann |
| 3,505,157 A | 4/1970 | Fields et al. |
| 3,515,778 A | 6/1970 | Fields et al. |
| 3,542,615 A | 11/1970 | Dobo et al. |
| 3,632,269 A | 1/1972 | Doviak et al. |
| 3,666,609 A | 5/1972 | Kalwaites et al. |
| 3,692,618 A | 9/1972 | Dorschner et al. |
| 3,694,867 A | 10/1972 | Stumpf |
| 3,814,052 A | 6/1974 | Caratsch |
| 3,881,381 A | 5/1975 | Kalwaites |
| 3,899,803 A | 8/1975 | Brumlik |
| 3,913,510 A | 10/1975 | Larsen |

(Continued)

FOREIGN PATENT DOCUMENTS

EP    0 096 458    12/1983

(Continued)

OTHER PUBLICATIONS

Encyclopedia of Chemical Technology, vol. 6 (1979), Wiley-Interscience Publication, Third Edition, pp. 388-389.

*Primary Examiner*—Alexander Thomas

(57) ABSTRACT

There is provided an elastic laminate of a base layer with one or more attached elastic elements forming an elastic region. The elastic region width varies from a terminal end of the elastic tab to a proximal end of the elastic tab such that a width adjacent the terminal end is 20 to 80 percent narrower than a width adjacent the proximal end. The elastic region is defined by a plurality of segments, having differing average widths in the length direction of the elastic tab elastic region. The one or more elastic elements vary in one or more properties such that a plurality of the segments having different widths have substantially the same degree of elongation at a given elongation of the shaped elastic tab laminate.

25 Claims, 3 Drawing Sheets

U.S. PATENT DOCUMENTS

| | | |
|---|---|---|
| 4,062,995 A | 12/1977 | Korpman |
| 4,183,121 A | 1/1980 | Cousins |
| 4,223,059 A | 9/1980 | Schwarz |
| 4,329,309 A | 5/1982 | Kelly |
| 4,340,563 A | 7/1982 | Appel et al. |
| 4,343,260 A | 8/1982 | Yajima et al. |
| 4,381,326 A | 4/1983 | Kelly |
| 4,573,991 A | 3/1986 | Pieniak et al. |
| 4,643,130 A | 2/1987 | Sheath et al. |
| 4,661,389 A | 4/1987 | Mudge et al. |
| 4,732,800 A | 3/1988 | Groshens |
| 4,753,838 A | 6/1988 | Kimura et al. |
| 4,842,596 A | 6/1989 | Kielpikowski et al. |
| 4,887,339 A | 12/1989 | Bellanger |
| 4,906,492 A | 3/1990 | Groshens |
| 4,935,287 A | 6/1990 | Johnson et al. |
| 4,965,122 A | 10/1990 | Morman |
| 4,981,747 A | 1/1991 | Morman |
| 4,984,339 A | 1/1991 | Provost et al. |
| 5,019,071 A | 5/1991 | Bany et al. |
| 5,028,646 A | 7/1991 | Miller et al. |
| 5,077,870 A | 1/1992 | Melbye et al. |
| 5,114,781 A | 5/1992 | Morman |
| 5,116,563 A | 5/1992 | Thomas et al. |
| 5,116,662 A | 5/1992 | Morman |
| 5,156,793 A | 10/1992 | Buell et al. |
| 5,167,897 A | 12/1992 | Weber et al. |
| 5,226,992 A | 7/1993 | Morman |
| 5,230,851 A | 7/1993 | Thomas |
| 5,260,015 A | 11/1993 | Kennedy et al. |
| 5,300,057 A | 4/1994 | Miller et al. |
| 5,326,415 A | 7/1994 | Thomas et al. |
| 5,385,706 A | 1/1995 | Thomas |
| 5,389,438 A | 2/1995 | Miller et al. |
| 5,399,219 A | 3/1995 | Roessler et al. |
| 5,441,687 A | 8/1995 | Murasaki et al. |
| 5,454,801 A | 10/1995 | Lauritzen |
| 5,458,590 A | 10/1995 | Schleinz et al. |
| 5,462,708 A | 10/1995 | Swenson et al. |
| 5,464,401 A | 11/1995 | Hasse et al. |
| 5,470,424 A | 11/1995 | Isaac et al. |
| 5,490,457 A | 2/1996 | Boulanger et al. |
| 5,496,298 A | 3/1996 | Kuepper et al. |
| 5,501,679 A | 3/1996 | Krueger et al. |
| 5,503,076 A | 4/1996 | Yeo |
| 5,531,729 A | 7/1996 | Coles et al. |
| 5,576,090 A | 11/1996 | Suzuki |
| 5,578,344 A | 11/1996 | Ahr et al. |
| 5,679,302 A | 10/1997 | Miller et al. |
| 5,685,758 A | 11/1997 | Paul et al. |
| 5,685,873 A | 11/1997 | Bruemmer |
| 5,705,013 A | 1/1998 | Nease et al. |
| 5,755,015 A | 5/1998 | Akeno et al. |
| 5,792,411 A | 8/1998 | Morris et al. |
| 5,827,579 A | 10/1998 | Groshens |
| 5,843,057 A | 12/1998 | McCormack |
| 5,868,987 A | 2/1999 | Kampfer et al. |
| 5,885,686 A | 3/1999 | Cederblad et al. |
| 5,899,895 A | 5/1999 | Robles et al. |
| 5,916,207 A | 6/1999 | Toyoda |
| 5,938,652 A | 8/1999 | Sauer |
| 5,948,707 A | 9/1999 | Crawley |
| 5,953,797 A | 9/1999 | Provost et al. |
| 5,983,467 A | 11/1999 | Duffy |
| 6,030,373 A | 2/2000 | VanGompel et al. |
| 6,039,911 A | 3/2000 | Miller et al. |
| 6,054,091 A | 4/2000 | Miller et al. |
| 6,074,505 A | 6/2000 | Ouellette et al. |
| 6,090,234 A | 7/2000 | Barone et al. |
| 6,093,663 A | 7/2000 | Ouellette et al. |
| 6,132,411 A | 10/2000 | Huber et al. |
| 6,132,660 A | 10/2000 | Kampfer |
| 6,190,594 B1 | 2/2001 | Gorman et al. |
| 6,200,299 B1 | 3/2001 | Heki |
| 6,255,236 B1 | 7/2001 | Cree et al. |
| 6,261,278 B1 | 7/2001 | Chen et al. |
| 6,264,639 B1 | 7/2001 | Sauer |
| 6,287,665 B1 | 9/2001 | Hammer |
| 6,336,922 B1 | 1/2002 | VanGompel et al. |
| 6,340,782 B1 | 1/2002 | Kling et al. |
| 6,406,466 B1 | 6/2002 | Pozniak et al. |
| 6,456,073 B2 | 9/2002 | Uetake et al. |
| 6,638,605 B1 | 10/2003 | Ankuda, Jr. et al. |
| 6,875,710 B2 | 4/2005 | Eaton |
| 6,939,334 B2 | 9/2005 | Odorzynski et al. |
| 6,942,894 B2 | 9/2005 | Alberg |
| 6,962,635 B2 | 11/2005 | Tuman |
| 7,037,457 B2 | 5/2006 | Seidel |
| 2001/0016245 A1 | 8/2001 | Tuman |
| 2002/0016551 A1 | 2/2002 | Selvester et al. |
| 2002/0018237 A1 | 2/2002 | Okada et al. |
| 2002/0019616 A1 | 2/2002 | Thomas |
| 2002/0115972 A1 | 8/2002 | Dabi et al. |
| 2002/0190418 A1 | 12/2002 | Jens et al. |
| 2003/0084996 A1 | 5/2003 | Alberg et al. |
| 2003/0085485 A1 | 5/2003 | Seidel et al. |
| 2003/0087059 A1 | 5/2003 | Jackson et al. |
| 2003/0087098 A1 | 5/2003 | Eaton et al. |
| 2003/0088220 A1 | 5/2003 | Molander et al. |
| 2003/0088228 A1 | 5/2003 | Desai et al. |
| 2003/0091807 A1 | 5/2003 | Desai et al. |
| 2003/0111166 A1 | 6/2003 | Uitenbroek et al. |
| 2004/0178544 A1 | 9/2004 | Jackson |
| 2004/0180186 A1 | 9/2004 | Jackson |
| 2004/0222553 A1 * | 11/2004 | Desai et al. ............ 264/171.24 |
| 2005/0142331 A1 | 6/2005 | Anderson |
| 2005/0191460 A1 | 9/2005 | Belau |

FOREIGN PATENT DOCUMENTS

| | | |
|---|---|---|
| EP | 0 189 351 | 7/1986 |
| EP | 0 580 073 | 1/1994 |
| EP | 0 830 930 | 3/1998 |
| EP | 0 892 320 | 1/1999 |
| FR | 1117251 | 5/1956 |
| FR | 2184741 | 12/1973 |
| TW | 355678 | 1/1998 |
| WO | WO 95/03723 | 2/1995 |
| WO | WO 96/10481 | 4/1996 |
| WO | WO 99/10166 | 3/1999 |
| WO | WO 00/07532 | 2/2000 |
| WO | WO 00/20200 | 4/2000 |
| WO | WO 00/50229 | 8/2000 |
| WO | WO 01/47697 | 7/2001 |
| WO | WO 01/68019 | 9/2001 |
| WO | WO 01/71080 | 9/2001 |
| WO | WO 02/00412 | 1/2002 |

* cited by examiner

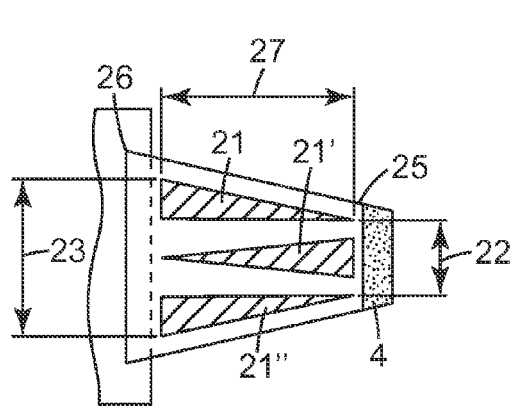
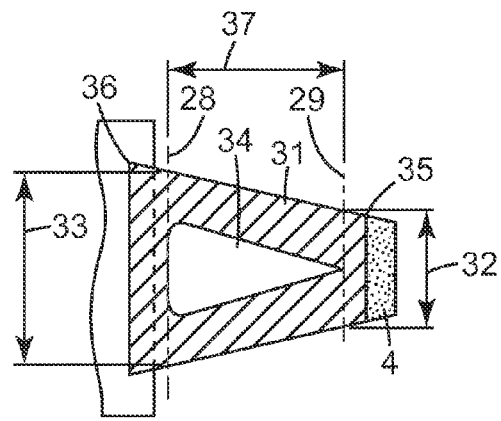
Fig. 5a
Fig. 6a
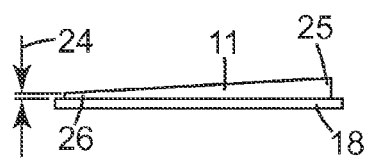
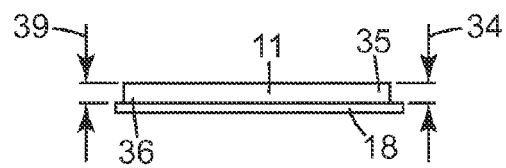
Fig. 5b
Fig. 6b
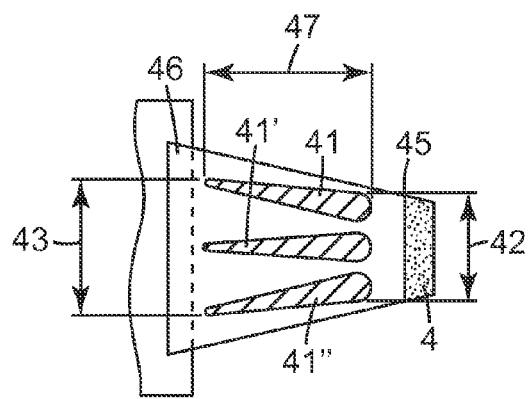
Fig. 7a
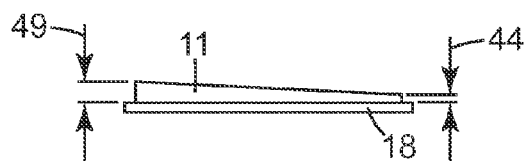
Fig. 7b

SHAPED ELASTIC TAB LAMINATES

FIELD OF THE INVENTION

The invention is directed at a shaped elastic tab laminate for use in an elastic fastening tab or element. The elastic fastening tab or element is designed to provide conformable fit when used as a closure tab on an article, which articles are generally disposable articles such as diapers, gowns, wraps or the like.

BACKGROUND OF THE INVENTION

Elastic has been used extensively in disposable articles such as diapers to create a more comfortable and secure fit, being used primarily along the legs and the waist. An example of a specific design of a waist area elastic is taught in U.S. Patent Application. No 2002/0165516, by Datta et al., which teaches a disposable diaper with a stretchable outer cover, wherein the stretchable outer cover can be configured to provide zones with different levels of level of elongation when subjected to a tensile force.

U.S. Pat. No. 6,456,073, to Morman et al. teaches a stretchable nonwoven web, or laminate of a stretchable nonwoven web and an elastic sheet that is treated with a plurality of bond lines in one or more regions thereof to provide controlled stretching properties. The use of the bond lines reduces the stretchability of the material in the region of the bond lines. This elastic can be used in various regions of a disposable article such as a diaper.

U.S. Pat. No. 6,200,299 to Y. Heki, teaches a disposable diaper with ear parts capable of distributing applied tensile forces around the waist and around the legs to prevent leakage. The elastic distributes forces but provides uneven tension along its length U.S. Pat. No. 6,336,922 to Van Gompel et al. teaches an absorbent article which includes a fit panel located in the waist region and extending laterally beyond the side edges of the chassis of the article. The fit panel may include a center bridge panel and a pair of laterally opposed side panels wherein the bridge panel and the side panels provide individual zones of elasticity across the width of the fit panel which have different elastic properties.

U.S. Pat. No. 6,264,639 and U.S. Pat. No. 5,938,652, both to B. A. Sauer, teaches an absorbent article, like a diaper, with a waist flap which includes a central zone and a pair of laterally opposed side zones which extend laterally outward from the central zone to the side edges of the absorbent article. Also taught is that the waist flap may include two or more different materials which may be joined together or otherwise arranged to provide different portions of the waist flap with different characteristic or properties, such as different elastic properties.

U.S. Pat. No. 6,132,411, issued to Huber, et. al., teaches absorbent articles, such as diapers, that have a side panel that have a low extension force leg zone and a high extension force waist zone to improve the overall fit of the article as well as reduce red marking on the wearer's skin.

U.S. Pat. No. 5,685,873 to M. A. Bruemmer, teaches a disposable diaper which includes a pair of differentially stretchable ear members which comprise a stretchable inner ear portion and a stretchable outer ear portion wherein these portions of the ears have different stretch characteristics. One method taught to achieve this is to shape the ears with converging tapered sides. Another way to achieve this in non-tapering ears is to use two different stretchable materials having different stretch characteristic. Also taught is using a single material and modifying the stretch characteristics in an area by using bonding lines or points as taught in U.S. Pat. No. 6,456,073 discussed above.

U.S. Pat. No. 5,496,298 to Kuepper et. al. teaches an elastomeric ear suitable for use on a disposable diaper. The elastomeric ear is formed from an elastomeric material which defines a proximal edge, a distal edge, a first connecting edge and a second connecting edge. The first and second connecting edges connect the proximal and distal edges. The second connecting edge is non-parallel to the first connecting edge, and the proximal edge is longer than the distal edge.

U.S. Pat. No. 5,464,401 to Hasse et. al. teaches a unitary disposable garment, such as a disposable training pant, having a high degree of stretch in the cross-machine direction and fitting a broad range of wearer sizes. The chassis from which the garment is manufactured, has four elasticized ear flaps, each ear flap is elasticized by securing an elastomeric element thereto and mechanically stretching the ear flap and the elastomeric element such that the ear flap is elastically extensible in the direction of initial stretching. It is also taught that the elasticized ear flaps may also be provided with differential extensibility along the longitudinal axis when stretched in the lateral direction. It is also taught that this differential extensibility can be achieved in a number of different ways, including that the ear flaps can have multiple combined elastomeric materials, multiple configurations for the elastomeric materials, or the extension properties of the elastomeric material or materials making up the elasticized ear flap may be non-uniform.

U.S. Pat. No. 5,156,793 to Buell et. al. teaches a "zero strain" stretch laminate web exhibiting a non-uniform degree of elasticity, as measured in the direction of web stretching at various points along an axis oriented substantially perpendicular to the direction of web stretching.

SUMMARY OF THE INVENTION

A shaped elastic tab is formed from an elastic laminate of a base layer with one or more attached elastic elements forming an elastic region. The elastic region width varies from a terminal end of the elastic tab to a proximal end of the elastic tab such that a width adjacent the terminal end is 20 to 80 percent narrower than a width adjacent the proximal end. The elastic region is defined by a plurality of segments, having differing average widths in the length direction of the elastic tab elastic region. The one or more elastic elements vary in one or more properties such that a plurality of the segments having different widths have substantially the same degree of elongation at a given elongation of the shaped elastic tab laminate.

BRIEF DESCRIPTION OF THE DRAWINGS

The present invention will be further described with reference to the accompanying drawings wherein like reference numerals refer to like parts in the several views, and wherein:

FIG. 2a is a side view of the elastic region of the shaped elastic tab laminate of FIG. 1a.

FIG. 4a is a side view of the elastic region of the shaped elastic tab laminate of FIG. 3a.

FIG. 5a is second embodiment top view of a shaped elastic tab laminate using an elastic laminate in accordance with the invention.

FIG. 5b is a side view of the elastic region of the shaped elastic tab laminate of FIG. 5a.

FIG. 6a is third embodiment top view of a shaped elastic tab laminate using an elastic laminate in accordance with the invention.

FIG. 6b is a side view of the elastic region of the shaped elastic tab laminate of FIG. 6a.

FIG. 7a is fourth embodiment top view of a shaped elastic tab laminate using an elastic laminate in accordance with the invention.

FIG. 7b is a side view of the elastic region of the shaped elastic tab laminate of FIG. 7a.

DETAILED DESCRIPTION OF THE INVENTION

Figure 1A:
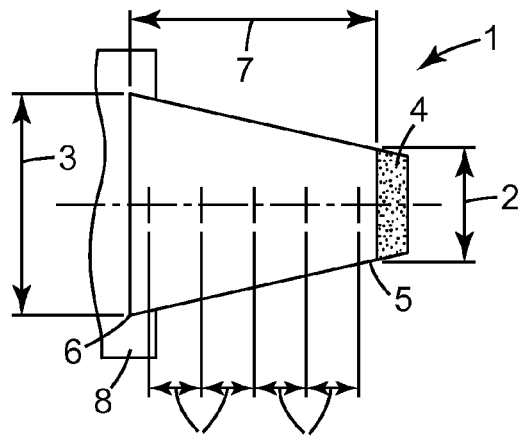
FIG. 1a is a top view of a shaped elastic tab laminate using a conventional elastic laminate.

A conventional type of shaped elastic tab or ear laminate 1 is shown in FIGS. 1a-2b. The elastic tab laminate 1 has a proximal end 6 that is attached to an article 8 where the proximal end 6 has a wide width 3. The elastic tab laminate 1 also has a terminal end 5, which generally is supplied with a fastener and which has a width 2 narrower than width 3 of the proximal end 6. A fastener 4 can be attached directly to terminal end 5 of the elastic tab laminate 1, as shown, or in some cases a further fastening tab could be attached to the terminal end 5 of the elastic tab laminate 1. The fastener 4 could be any conventional fastener such as an adhesive, or a hook or loop mechanical fastener.

Figure 1B:
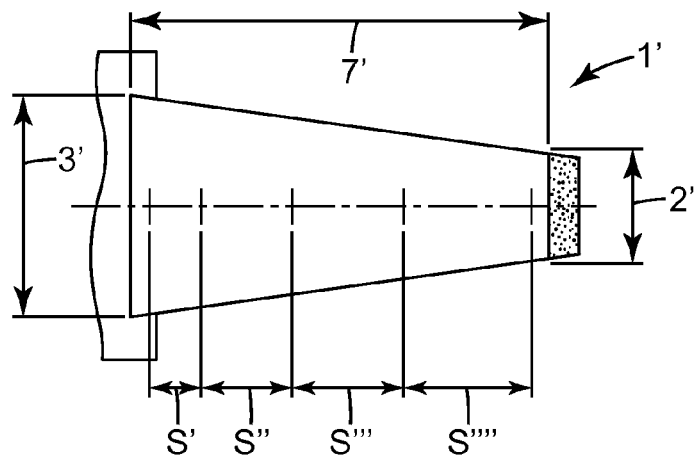
FIG. 1b is a top view of the shaped elastic tab laminate of FIG. 1a when elongated.
Figure 2A:
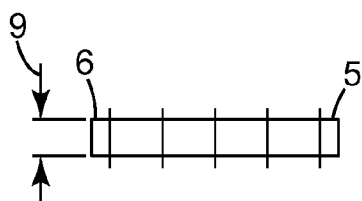
Figure 2B:
FIG. 2b is a side view of the elastic region of the shaped elastic tab laminate of FIG. 1a when elongated as shown in FIG. 1b.

A conventional shaped elastic tab laminate 1 is divided artificially into equal segments S for illustration of the elastic properties along the length 7 of the elastic region of the elastic tab laminate 1. The conventional elastic tab 1 elastic element cross section is shown in FIG. 2a, where the elastic element is shown having a relatively constant thickness 9. This elastic element would conventionally be an elastic film material. This conventional type of tab 1 when stretched will elongate to a length 7', as shown in FIG. 1b. Each of the initially equal length segments S will elongate to a different extent. Namely the tensioned segments S', S", S''', S'''' etc. will all be different lengths with the segments S having the narrowest average widths elongating the most. In FIG. 1a, 7 is the initial length of the elastic region and in FIG. 1b 7' is the length of the elastic region as stretched or elongated. The elastic film in the tab 1 will have a cross sectional profile in the stretched or elongated state 7' as shown in FIG. 2b where the thickness will vary depending on the extent that a particular incremental segment stretches.

A shaped elastic tab, as shown in FIG. 1a, is desirable to provide a distribution of forces over a wide area at the proximal end 6 (the tension applied at terminal end 5 is distributed to the wider proximal end 6) but a large portion of the elastic tension is concentrated at the terminal end 5 which creates the potential for red markings, while ineffectively utilizing a majority of elastic material forming the elastic element of the elastic tab laminate.

Generally, the elastic tab laminate of the invention comprises an elastic laminate of a base layer or layers with one or more attached elastic elements. The base layer is generally an inelastic but extensible material, such as a fibrous web or film. The base is generally a nonwoven fibrous web such as a spunbond web, a melt blown web, a carded web, a spunlace web or the like, which nonwoven fibrous web is extensible under the forces normally used by a person applying a disposable absorbent article The base is generally a continuous base without cutouts between separate elastic elements.

The elastic elements form at least one elastic portion or region on the tab laminate where the width of the elastic region of the elastic tab laminate, and preferably one or more of the elastic elements forming the elastic region, varies in this elastic region. The elastic elements are preferably film or film-like elastic materials.

The elastic region can be defined by a multitude of arbitrary elastic segments S along an axial centerline of the tab laminate where the width and/or thickness and/or activation level of the elastic elements, in these segments, varies inversely to the width of the elastic laminate, such that a plurality of the elastic segments S have substantially the same degree of elongation at a given overall elongation of the elastic tab. These elastic segments S will vary in width. Generally, these elastic segments S elongate to within plus or minus 30 percent of each other, preferably 1 to 20. In a particular arrangement three or more, or four or more, five or more, or even all possible, elastic segments S are elongated to within 1 to 20 or percent or 1 to 10 percent of each other at a given elongation of the elastic tab. For purposes of definition, each of the elastic segments is 10 percent or more of the elastic region, preferably 10 to 30 percent of the elastic region and are at least 2 mm wide. The elastic segments can sometimes be separated by small inelastic segments or segments with less elasticity, in this case the elastic segments having substantially the same degree of elongation at a given elongation of the elastic tab can be separated by 1 to 10 mm, or 1 to 5 mm.

One way to achieve the above constant elastic properties for the elastic segments is for one or more of the elastic elements to vary in their thickness, so as to provide elastic segments having substantially the same degree of elongation (as defined above) at a given elongation of the elastic tab. For example, assume that one elastic element is provided where the width of the elastic tab laminate and the attached elastic element is x at one point (a) and 1.5x at a second point (b) within a given elastic segment or the elastic region as a whole. With this variation in the elastic tab laminate width the elastic element provided would generally have a thickness of 1.5y at the first point (a) and y at the second point (b), with the same ratio applying at points in between points (a) and (b). This provides a laminate with relatively the same cross sectional amount of elastic material at the these two points (and the points in between, if this same relationship is maintained), which in turn can provide a relatively constant degree of elongation despite the variation on the width of the elastic tab laminate and/or the attached elastic element. This assumes that the elastic laminate base layer is generally equally extensible in all relevant elastic segments of the elastic tab laminate.

Figure 3A:
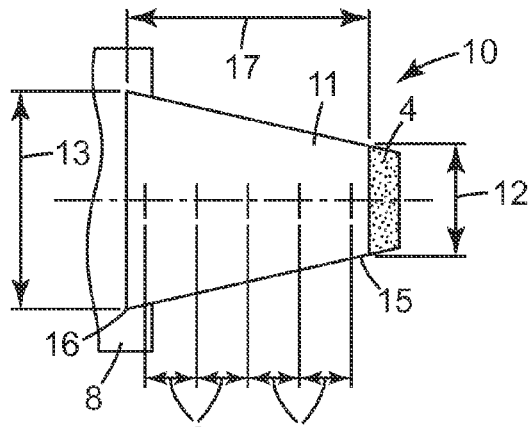
FIG. 3a is a top view of a shaped elastic tab laminate using an elastic laminate in accordance with the invention.
Figure 3B:
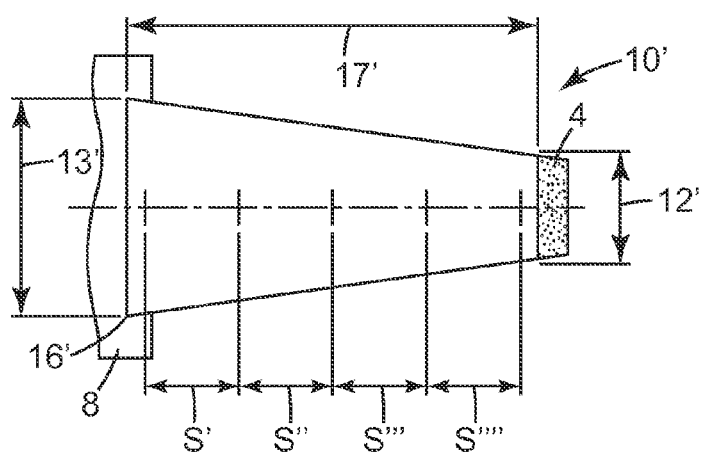
FIG. 3b is a top view of the shaped elastic tab laminate of FIG. 3a when elongated.

FIG. 3a is an elastic tab laminate 10 of the invention. The elastic element 11 can likewise be a film elastic or could also be nonwoven elastic or other types of film-like elastics. The elastic tab laminate has a proximal end 16 that is attached to an article 8, where the proximal end 16 of the elastic portion 17 of the tab (in this case the entire tab excluding the portion with the fastener 4) has a width 13. The tab 10 also has a terminal end 15, which as shown is supplied with a conventional fastener 4 directly attached to the tab 10 terminal end 15. This portion of the tab 10 where the fastener is attached would preferably not be elastic, either due to the tab material being inelastic in this area or due to the attached fastener or both. The tab terminal end 15, where the elastic portion or region terminates, has a width 12 which in general is at least 20 to 80 or 30 to 60 percent narrower than the elastic portion or region proximal end width 13. The elastic region can then be subdivided into a plurality of elastic segments S which vary in average width along the length of the elastic region. Each segment S would have an average width defined as the average width value for that segment.

Figure 4A:
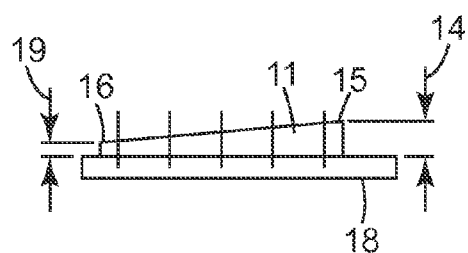
Figure 4B:
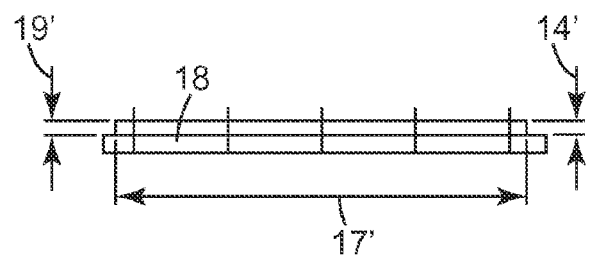
FIG. 4b is a side view of the elastic region of the shaped elastic tab laminate of FIG. 3a when elongated as shown in FIG. 3b.

In the specific embodiment of FIG. 3a-4b the elastic tab laminate 10 is shown as a laminate of a single elastic element or material 11, which is laminated to a continuous substrate 18. The elastic element 11 is a film or film-like material where the material thickness 19, 14 varies inversely to the width of the elastic region of the elastic tab. This is seen in FIG. 4a where the thickness 19 at the proximal end 16 is less than the thickness 14 at the terminal end 15. Generally the thickness of the elastic material 11 multiplied by its width, for any given cross section or predetermined segment, is either a relatively constant cross sectional area or volume, respectively. The result is when the elastic tab 10 is elongated 10' in the elastic region, from a length of 17 to a length 17', the elongated segments (S', S'', S''', S'''' etc.) are all relatively the same length while the thickness 19' and 14' of the elastic material will tend to become more uniform as shown in FIG. 4b.

In a second embodiment of the invention as shown in FIGS. 5a and 5b multiple elastic elements 21, 21' and 21" are provided that also vary in thickness, as in the FIG. 3a-4b embodiment. The three elastic elements 21, 21' and 21" define an elastic region that has a width 23 at the proximal end 26 and a width 22 at the terminal end 25 of the tab. In other respects this embodiment is similar to that of FIGS. 3a to 4b. The elastic in this case could be applied as described in US Patent No 2003/0087059, the substance of which is incorporated by reference in its entirety. In this method thermoplastic elastic is deposited onto a substrate 18 from a surface, such as a roll, that has thermoplastic elastic deposited (such as by extrusion) into depressions on the surface, which depressions define the shape of the elastic elements being formed. The thermoplastic elastic in the depressions is transferred to a substrate 18 generally by thermal bonding of the elastic to the substrate, but could also be adhesively transferred at least in part. The elastic element can also be applied by adhesives or conventional lamination techniques.

The elastic laminates can also vary in the degree of extensibility of the base materials to control the elastic behavior of the laminate. This would generally be done by attaching the elastic elements to the base while in an unextended form and then subjection the laminate to varying degrees of activation to aid in providing elastic segments having the constant stretch characteristics described above. Activation could be done in this manner by using a variable incremental stretching device. This would be a device that would activate very small incremental areas of the laminate more or less independent of each other. This technique is also known as ring rolling. The teeth forming the gears can be of varying sizes and shapes. Generally deeper intermeshing gears will result in higher levels of activation so a more highly activated section will extend easier than a less activated section, which can be used in whole or in part to provide a plurality of elastic segments having substantially the same degree of elongation at a given elongation of the elastic tab as discussed above.

Another way to achieve the above constant elastic properties (elastic segments having substantially the same degree of elongation at a given elongation of the elastic tab) is with elastic elements that vary in their shape. This could be done as shown in the embodiment of FIGS. 6a and 6b. The elastic region 37 with elastic segments having relatively constant elongation properties is that portion between the two dashed lines 28 and 29. This elastic region 37 will have a width 32 near the terminal end 35 of the tab and a width 33 near the proximal end of the tab. The elastic cutout 34 is a portion of the elastic region 37 provided with no elastic or a nominal elastic skin, but an underlying base 18 in the elastic cutout region 34. The elastic material 31 widens as it goes from the terminal end 35 to the proximal end 36 but a relatively constant amount of elastic material in the cross section of the elastic region 37 is maintained by the cutout region 34, where the width of the cutout region corresponds to the width of the elastic region. The elastic 11 in this embodiments is a constant thickness.

FIG. 7a shows further embodiment of an elastic region 47 where thickness is used to vary the elongation properties of elastic elements 41, 41' and 41" where elastic region 47 width varies from a width 42 at the terminal end 45 to a width 43 at the proximal end 46 to provide a elastic region 47 with relatively constant elongation. The width of the elastic elements 41, 41' and 41" vary inversely with the width of the tab, this requires that the thickness of the elastic elements 49 and 44 varies in the opposite manner.

Generally the elastic region whether formed by one or a multiple of elastic elements is from 15 to 400 mm in length, or 20 to 200 mm, and varies in width between the terminal end to the proximal end (or some portion thereof) by at least 20 percent, or 30 percent, from it's minimum to maximum width. In most arrangements it is best if the elastic region tapers continuously from an outer portion (the terminal end) to an inner portion (the proximal end). This creates a contoured side shape that conforms to the wearer, this taper could be linear but also other shapes such as parabolic. To provide for attachment of the elastic tab to an article or attachment of standard fastening elements to the tab laminate, such as hook or loop mechanical type fasteners or pressure sensitive adhesives the elastic region can be joined to an least one inelastic region. The inelastic region could be part of the same laminate but created by an inelastic substrate, a deactivation of the elastic, a reinforcing strip or the like.

The invention elastic tab laminate is generally used as a side closure element or an ear for a disposable absorbent article such as a diaper or adult incontinent article. The shaped elastic region distributes the force from the outer terminal end to a proximal end attached to the diaper or the like, however the elastic elongates evenly avoiding high and low tension segments s in the elastic region.

We claim:

1. A shaped elastic tab comprising an elastic laminate of a continuous base layer with one or more attached elastic elements, forming an elastic region, where the width of the elastic region varies from a terminal end of the elastic tab to a proximal end of the elastic tab such that the terminal end width is 20 to 80 percent narrower than the proximal end width, the elastic region being defined by a plurality of elastic segments, having differing average widths in the length direction of the elastic tab elastic region, the one or more elastic elements varying in one or more properties such that a plurality of the elastic segments having different widths have substantially the same degree of elongation at a given elongation of the elastic tab.

2. The elastic tab of claim 1 wherein the elastic region terminal end width is 30 to 60 percent narrower than the elastic region proximal end width.

3. The elastic tab of claim 1 wherein each of the elastic segments is at least 10 percent of the elastic region.

4. The elastic tab of claim 3 wherein each of the elastic segments is 10 to 30 percent of the elastic region.

5. The elastic tab of claim 3 wherein each of the elastic segments is at least 2mm wide.

6. The elastic tab of claim 5 wherein two or more elastic segments have substantially the same degree of elongation at a given elongation of the elastic tab.

7. The elastic tab of claim 5 wherein five or more elastic segments have substantially the same degree of elongation at a given elongation of the elastic tab.

8. The elastic tab of claim 5 wherein the elastic region is from 15 to 400 mm in length.

9. The elastic tab of claim 5 wherein the elastic region is from 20 to 200 mm in length.

10. The elastic tab of claim 5 wherein the elastic region varies in width from it minimum to maximum width by at least 20 percent.

11. The elastic tab of claim 5 wherein the elastic region varies in width from it minimum to maximum width by at least 30 percent.

12. The elastic tab of claim 5 wherein the elastic region tapers continuously from an outer portion to an inner portion.

13. The elastic tab of claim 5 wherein the elastic region is joined to at least one inelastic region.

14. The elastic tab of claim 13 wherein the inelastic region has a fastener element.

15. The elastic tab of claim 14 wherein the inelastic region fastener element is a mechanical fastener.

16. The elastic tab of claim 3 where the elastic segments elongate to within plus or minus 30 percent of each other.

17. The elastic tab of claim 3 where the elastic segments elongate to within plus or minus 1 to 20 percent of each other.

18. The elastic tab of claim 1 wherein one or more of the elastic elements vary in their cross sectional dimensions to provide the plurality of elastic segments having substantially the same degree of elongation at a given elongation of the elastic tab.

19. The elastic tab of claim 1 wherein one or more of the elastic elements vary in their thickness to provide the plurality of elastic segments having substantially the same degree of elongation at a given elongation of the elastic tab.

20. The elastic tab of claim 1 wherein one or more of the elastic elements vary in their degree of activation to provide the plurality of elastic segments having substantially the same degree of elongation at a given elongation of the elastic tab.

21. The elastic tab of claim 1 wherein the base layer extends continuously between any separated elastic elements.

22. The elastic tab of claim 1 wherein there is at least one elastic segment having a different elongation, at a given elongation of the elastic tab than the other elastic segments.

23. The elastic tab of claim 1 wherein the base layer is a fibrous web.

24. The elastic tab of claim 1 wherein the base layer is a nonwoven fibrous web.

25. The elastic tab of claim 24 wherein the one or more elastic elements are laminated between two nonwoven fibrous base layers.

* * * * *